United States Patent
Gagna

(10) Patent No.: US 6,936,461 B2
(45) Date of Patent: Aug. 30, 2005

(54) METHOD FOR IMMOBILIZING MULTISTRANDED NUCLEIC ACID MOLECULES BY MODIFYING MORE THAN ONE STRAND THEREOF, AND BINDING EACH STRAND TO A SOLID SUPPORT

(75) Inventor: Claude Gagna, Old Westbury, NY (US)

(73) Assignee: New York Institute of Technology, Old Westbury, NY (US)

( * ) Notice: Subject to any disclaimer, the term of this patent is extended or adjusted under 35 U.S.C. 154(b) by 0 days.

(21) Appl. No.: 10/209,849

(22) Filed: Jul. 31, 2002

(65) Prior Publication Data

US 2003/0096273 A1 May 22, 2003

Related U.S. Application Data

(60) Provisional application No. 60/308,936, filed on Jul. 31, 2001.

(51) Int. Cl.[7] ............................. C12Q 1/68; C07H 21/04
(52) U.S. Cl. .......................... 435/287.2; 435/6; 436/94; 422/101
(58) Field of Search .......................... 435/6, 7.1, 287.2; 436/94; 422/101

(56) References Cited

U.S. PATENT DOCUMENTS

| | | | | |
|---|---|---|---|---|
| 5,055,316 A | * | 10/1991 | Hoffman et al. | 530/359 |
| 5,591,841 A | * | 1/1997 | Ji et al. | 536/25.4 |
| 5,624,803 A | * | 4/1997 | Noonberg et al. | 435/6 |
| 5,726,050 A | * | 3/1998 | Rich et al. | 435/455 |
| 5,763,768 A | * | 6/1998 | Henderson et al. | 73/105 |
| 5,958,701 A | * | 9/1999 | Green et al. | 435/6 |
| 6,147,198 A | * | 11/2000 | Schwartz | 536/23.1 |
| 6,187,537 B1 | * | 2/2001 | Zinn et al. | 435/6 |
| 6,420,112 B2 | * | 7/2002 | Balhorn et al. | 435/6 |

* cited by examiner

Primary Examiner—Kenneth R. Horlick
(74) Attorney, Agent, or Firm—Fulbright & Jaworski LLP

(57) ABSTRACT

Various methodologies for the immobilization of molecules such, as multistranded nucleic acid molecules, are described. The methodologies include activation of solid supports, as well as treatment of, e.g. termini of nucleic acid molecules to render them more receptive to immobilization on surfaces.

35 Claims, No Drawings

SEQUENCE LISTING

<160> NUMBER OF SEQ ID NOS: 1

<210> SEQ ID NO 1
<211> LENGTH: 15
<212> TYPE: DNA
<213> ORGANISM: Artificial sequence
<220> FEATURE:
<221> NAME/KEY: misc_structure
<223> OTHER INFORMATION: Other information
      stabilizer for quadruplex DNA

<400> SEQUENCE: 1
ggttggtgtg gttgg                                                   15

METHOD FOR IMMOBILIZING MULTISTRANDED NUCLEIC ACID MOLECULES BY MODIFYING MORE THAN ONE STRAND THEREOF, AND BINDING EACH STRAND TO A SOLID SUPPORT

RELATED APPLICATION

This is a continuation in part of application Ser. No. 60/308,936, filed Jul. 31, 2001, incorporated by reference.

FIELD OF THE INVENTION

This invention relates to methods for the immobilization of molecules to solid phases. In preferred embodiments, it relates to multistranded (i.e., at least 2 strands of nucleic acids) molecules which are immobilized to a solid phase. Once so immobilized, the molecules can be used in various assays, such as screening assays. Also a feature of the invention are the prepared solid phases used, to immobilize the molecules.

BACKGROUND AND PRIOR ART

The determination of the three-dimensional structure of ds (double stranded)-DNA, RNA and other non-traditional, intact nondenatured nucleic acids is extremely important for the understanding of their interactions with proteins as well as other biomolecules and nonbiomolecules involved in prokaryotic and eukaryotic regulation, gene expression and repair, among other fields. See Sanger, W. Principles of Nucleic Acid Structure. 1984, Springer-Verlag, NewYork; Sinden, R. R., 1994, DNA Structure and Function. pp. 1–398. Academic Press, NewYork; Sarma, R. H. Nucleic Acid Geometry and Dynamics. 1980, pp. 1–424. Pergamon Press; Zimmerman, S. B. Ann. Rev. Biochem. 1982; 51:395–427; Dickerson, R. E. 1983. Scientific American, 249(6):94–111, Dickerson, R. E. Methods in Enzym. 211:67–111, 1992; Rich, A. Ann. Rev. Biochem. 53:791–846, 1984). It is also important for the understanding of nondenatured nucleic acid reactions with molecules, such as drugs, that may block the correct reading of the nucleic acid molecule. Ds-DNA can undergo conformational fluctuations, such as helical changes resulting in changes from B- to Z-DNA. Curvature and bending of ds-DNA, and other nondenatured nucleic acid molecules can take place alone or when the molecules are complexed with other substances, such as a protein or plurality of proteins. Protein-DNA complexes can cause major conformational changes in the ds-DNA or RNA, such as sharp kinks and bending toward the major groove (J. Kim et al., 1993 Nature 365:512–520; J. L. Kim et al., 1993 Nature 365:520–527). For instance, human 170 KDa topoisomerase II binds preferentially to curved left-handed Z-DNA (J. Biomol. Struc. & Dyn. 12:605–623, 1994). Variant states and structures of DNA have biological and physical properties that differ from those of bulk DNA. Examples of such variant states include sites of base mismatches, DNA bulges, DNA-histone complexes, DNA sequences that induce bending of the helix axis, cruciforms, H-DNA and other branched species (Cooper, J. P. et al, Proc. Natl. Acad., Sci. USA 86:7336–7340, 1989), and so-called left-handed Z-DNA. Some of these states have been implicated in biological functions including mutagenesis, control of transcription and/or gene expression), or genetic recombination.

One of the approaches to assessing the biological role of high-energy forms of ds-DNA, such as Z-DNA, is to reveal such ambient conditions (e.g., pH, ionic strength, temperature, milieu polarity, high pressure, photodynamic damage, as would favor stabilization of alternative DNA (and other nucleic acid structures. Such studies, however, require a source of stable, immobilized molecules which can then be used for further study.

Microarrays, or solid phase structures containing hundreds or thousands of molecules affixed thereto, have become an important feature of molecular biology, especially in areas like genomics, and in screening arrays; however, the methods available to this point in time for immobilizing molecules generally, and nucleic acid molecules in particular, are limited. Especially limited are methods for immobilizing somewhat more uncommon form of nucleic acids including those which are in, e.g., Z conformation, multistranded molecules, such as nucleic acid molecules containing 2–10, preferably 2–6 strands and circular molecules, like plasmids, which may be supercoiled in whole or in part.

It is the aim of this invention to provide methods and apparatus that are useful in immobilizing such molecules, as well as assays which can be used with the resulting molecules.

How these features of the invention are achieved will be seen in the detailed disclosure which follows.

DETAILED DESCRIPTION OF PREFERRED EMBODIMENTS

The novel invention involves, inter alia, rapid and cost effective screening, using both spotted microarrays in which molecules, such as nucleic acid molecules, are pre-synthesized and then bound onto solid support surface (e.g., glass slides, plastic slides, nylon membranes or silicon) or high-density nucleic acid arrays, in which nucleic acid molecules are synthesized in situ on solid supports using a photolithigraphic process such as that described by Chee, M. Science, 27:610–614 (1996). It is preferred that the nondenatured nucleic acid molecules be synthesized externally, using known techniques and then be immobilized onto the solid support surface. The invention permits characterization of the physical and chemical properties of nondenatured molecules, such as nucleic acid molecules, as well as determination of nuclease hypersensitive sites, intact chromatin, sequence-directed curvature of ds-DNA, parallel-stranded DNA under topological stress, the helical periodicity of DNA, three-dimensional structures of substances interacting with nucleic acids, such as DNA/protein complexes, structural basis for ds-DNA binding, and many other structures of nondenatured nucleic acid molecules or other molecules.

Nucleic acid microarray methodologies are expected to dominated medicine in the future; however, there is continued interest in developments, lower cost and superior product offerings which may be made available to a wider audience of, e.g., molecular biologists, biopharmaceutical scientists, and so forth. The methods of the invention pave the way for more affordable and productive development of products, including ds-DNA and RNA, binding proteins, antibodies, transcription factors, endonuclease-labeled proteins, chiral metal molecular probes, drugs, chemicals, enzymes, etc. for use in, e.g. diagnostics, disease management and therapeutics. The invention provides the art with the ability to characterize different disease processes, including cell death, cell differentiation and aging, by permitting study of, e.g. age linked ds-DNA detiorization. It also allows for accurate and speedy protein profiling. Yet further, it allows for study of ds-DNA-protein complexes, RNA-protein complexes, DNA- or RNA drug, or protein-drug complexes, DNA-histone/drug complexes, protein-protein complexes, DNA-protein-drug complexes and a variety of other more complex multiple interactions. Nucleic acid molecule interactions involving many factors can also be studied, such as DNA-protein, or protein-drug interactions and competitive binding assays can also be performed.

Since temperature plays a role in maintaining and modifying nucleic acid helical structures, this inventive system can use different temperatures in combination with different cationic solutions to help characterize nucleic acid factors, such as proteins, which bind to the immobilized nondenatured nucleic acid molecules. Both normal and mutated proteins can be characterized extensively. Mutated nucleic acid binding proteins, with defects in the residues needed for specific recognition of, e.g., DNA binding proteins can be analyzed via the nondenatured nucleic acid microarray systems of the invention. The invention permits monitoring of the interactions of drugs such as inhibitory compounds as well as other factors, such as proteins, to different normal and mutated genes which are undergoing conformational transitions, such as helical transitions within specific environments. Exemplary of this are the transition of right-handed ds-B-DNA to left-handed ds-Z-DNA (4 M NaCl), and right-handed B-RNA to left-handed Z-RNA, (10 mM NaCl). Characterization of right-handed ds-B-DNA binding proteins can be made in solutions of low ionic strengths, such as 150 mM NaCl.

The helical transformation of ds-DNA plays a major role in eukaryotic and prokaryotic gene expression. The invention is useful in, e.g., the biopharmaceutical industry and development processes of other fields such as pharmacogenomics, toxocogenomics and human diagnostics.

The standard DNA microarray technology presently available, uses denatured ss-DNA oligonucleotides from cDNA libraries. Oligonucleotides are synthesized or placed directly on the solid support surface to study the gene expression of m-RNA isolated from a particular tissue under specific conditions (example: anti-cancer drug given to test animals). These standard DNA microarrays profile expressed genes via hybridization.

The invention permits the characterization of both the structure of a gene undergoing conformational changes, such as helical changes, which, e.g., regulate gene expression. For example, one can study transitioning ds-B-DNA to ds-Z-DNA and then back to ds-B-DNA and/or the interaction of the molecules with other substances, such as proteins, or non-protein drugs that might inhibit or enhance gene expression, such as Z-DNA binding proteins. Multiple factors can be studied simultaneously with the invention, if each nucleic acid probe has a different label attached to it.

Using the invention, ds-, or multiple-stranded nondenatured nucleic acids can be either placed directly onto the solid support surface, or synthesized onto the surface. Ds-DNA or RNA, triplex-DNA, quadruple-DNA, pentaplex-DNA, native DNAs, synthetic DNAs, activated DNAs and covalently closed ds-DNA plasmids may be immobilized onto a solid support using this invention.

A further aspect of the invention are immobilization techniques for use with, e.g., plasmid DNA. By using a variety of different ionic solutions (e.g., 150 mM, 500 mM, 750 mM, 1 M, 1.5 M, 2.0 M, 2.5 M, 3.0, 3.5 M, 4.0 M and 4.5 M NaCl), the investigator can characterize a nucleic acid binding factor such as a protein, an antibody, a drug, or a metal chiral probe, in terms of its interaction with an immobilized, nondenatured nucleic acid conformation. The nucleic acid binding factor may be used to carry a drug to a specific DNA site. An example of this is the use of an antibody with an anticancer drug attached, or it may directly turn off a gene, such as a DNA binding protein. Instead of placing thousands of denatured genes (cDNA) on the microarray, the invention places thousands of genes which are ds-DNA. Superior results are obtained when nucleic acid molecules of a particular conformation are placed directly on the surface, within the center of, e.g., the 400 μm spot.

A feature of the invention are immobilization procedure technologies, that can be used to bind and retain unlabeled ds-, and/or multiple-stranded nucleic acids on a solid phase within a specific environment (e.g., 150 mM NaCl solution) so as to characterize a nucleic acid probe such as a protein. Immobilization of, e.g., plasmids, and UV functionalized surfaces of modified, or scratched plastics which provide 3-dimensional surfaces are other features of the invention, which are described infra. The invention uses immobilized unlabeled nondenatured ds-nucleic acid molecules or multiple-stranded nucleic acid molecules on solid phases, such as glass or plastic slides which have been functionalized with, e.g. an aldehyde, a silicon/ceramic wafer, poly-L-lysine, a nylon membrane, a gel pad, etc. and then placed into a microcontainer which hold an ionic solution, which may change the nucleic acid conformation. The immobilized ds-nucleic acid molecules or multiple-stranded nucleic acid can then be used to characterized different nucleic acid binding factors by injecting a solution which maintains the right-handed ds-B-DNA conformation into the microcontainer of several microliters. Another option is to build microminiature laboratories on the slides, using several different injectable solutions (e.g., a microfluid chip) which interact with specific and isolated regions on the microarray surface. This makes it possible for users to move extremely small amounts of fluids via microscale canals on integrated microfluid devises. This allows for molecular biological reactions to occur on a micro-scale level. The solutions may increase in ionic strength gradually. For example, in studying B-DNA to Z-DNA transitions, one may use 150 mM, 450 mM, 1 M, 1.5 M, 2.0 M, 2.5 M, 3.0 M, 3.5 M and 4.0 M NaCl. This permits characterization of the gradual transition of, e.g., right-handed ds-B-DNA to left-handed ds-Z-DNA, within a specific gene, with known base pairs, while simultaneously examining its interaction with a specific nucleic acid binding factor. The biological and non-biological factors to be characterized, via their binding to different ds-, triple-stranded, four-stranded and five-stranded nucleic acids can be either directly or indirectly labeled and quantified with, e.g. fluorescent dyes, enzymes and so forth. Non-limiting examples of nucleic acid probes that can be used with this system are antibodies, proteins, chiral metal molecular probes, PicoGreen ds-DNA fluorescent probe, drugs, enzymes, transcription factors, etc. For example, a protein probe labeled with a fluorescent dye can then have its binding reaction to the immobilized nondenatured nucleic acid of known sequences or helical conformations (example: Z-DNA) quantified via its fluorescence. This technique can be used to characterize the binding reaction of drugs, chemicals, chiral metal molecular probes, ds-DNA PicoGreen probe, antibodies, DNA-(RNA) binding proteins, transcription factors, modeling the binding mechanisms of restriction enzymes and many other nucleic acid factors, towards the many different helical conformations of ds-DNA, ds-RNA, DNA-RNA hybrids, ss-DNA (ss-RNA), triplex-DNA, quadruple-DNA, pentaplex-DNA, and covalently closed circular ds-DNA plasmids, under a variety of different physiological which may resemble in vivo conditions, such as 150 mM NaCl, and non-physiological ionic strength ionic solutions, such as 4 M NaCl. These ionic solutions convert one helical conformation of an immobilized nucleic acid molecule into a slightly different or totally different helical conformation permitting structure-function analysis.

Just as critical as the helical conformation is the selection of base pairs, for either the gene, gene fragment or synthetic copolymer. The ds-, or multiple-stranded nucleic acids can be used to characterize both sequence-specific and non-sequence-specific proteins and/or protein binding sites. Some DNA-protein interactions require that the ds-DNA have a modification. The invention allows for the deposition of any type of biochemically modified ds-DNA (RNA) or multiple-stranded nucleic acid, such as methylated DNA, onto the solid support surface, which has been previously functionalized with, e.g., aldehyde or via coating with poly-L lysine. Thus, the nondenatured ds-, multiple-stranded nucleic acid structure-transition microarrays of the invention differ from microarrays found in the prior art.

Not only can the method screens of the invention be used in high throughput screens, but also in low throughput assays. It can be used to gain "broad-brush" understanding of complete genomes (e.g., ds-DNA; fragmented genomic DNA libraries) or, once a target site has been found, specific genes can then be further characterized. The binding capacity, and/or mechanism of drug such as radiochemicals with ds-DNA, ss-DNA, ds-RNA, ss-RNA, ds-B-DNA, Z-DNA, peptide DNA, protein-nucleic acids complexes, triplex-DNA, quadruple-DNA, covalently closed circular ds-DNA of plasmids and pentaplex-DNA structures, can all be investigated. Competitive binding assays can be used in the invention, i.e., in assays where two or more nucleic acid probes such as a putative known binding drug and protein) compete simultaneously for a ds-, or multiple-stranded nucleic acid molecule binding site. For example, different drugs and Z-DNA binding proteins can be tested together to characterize binding potential and to predict gene expression in response to drug treatments. The use of competitive binding can also be employed with two, three, four, five or more different factors, simultaneously.

Covalently closed circular plasmids (ds-DNA) can be used, e.g., to characterize nucleic acid factors such as DNA binding proteins or to characterize a newly discovered gene with an already characterized nucleic acid factor, such as known DNA transcription factor. Using a ds-DNA plasmid allows the investigator the ability to study DNA supercoiling and how this process affects the manner in which a nucleic acid factors binds to ds-DNA. Topoisomerases can be used in experiments designed to study DNA supercoiling in order to characterize the plasmid (with or without a gene)—nucleic acid probe interaction. Multiple-strategies can be employed, including competitive binding assays with and without the use of topoisomerases. The invention permits immobilization of covalently closed circular plasmids (ds-DNA). Additionally, triplex-DNA, quadruplex-DNA and pentaplex-DNA molecules can be incorporated into the plasmid for characterization under supercoiling conditions.

Many ds-oligonucleotides and synthetic polynucleotides have a length of about 20-mer. In the practice of the invention, longer oligonucleotides, for example oligomers of about 50-mers work better. Ds-oligonucleotides of from about 50-mer to about 70mer or more, produce the best overall results and allow a high signal intensity and high specificity.

In order to visualize the reaction of the ds-, or multiple-stranded nucleic acid with the nucleic acid probes, the probe must be labeled, either directly or indirectly. Fluorescence or radioactivity or other labels can be used, and multiplexing can also be employed for using several different probes simultaneously, each labeled with a different label, e.g., a fluor. With direct labeling, the nucleic acid probe is directly labeled itself. With indirect labeling a standard procedure, such as the biotin-avidin staining method is used. A scanning fluorescent microscope, or other system depending on the label, illuminates each spot and measures the fluorescence (or other signal) of each fluor separately.

DNA is a highly elastic macromolecule. It is also polymorphic and can assume a variety of different helical conformations (structures such as ds-A-DNA, ds-B-DNA and ds-Z-DNA). With some DNA interactions involving proteins, the ds-B-DNA helix is distorted and somewhat unwound. Ds-DNA has the physical ability to change from a relaxed state (right-handed ds-B-DNA) into a tensed state which, if measured, is longer. An example of this can sometimes occur with ds-, and/or multiple-stranded nucleic acids when attached to a functionalized solid support of a glass microarray slide.

The invention involves, inter alia, immobilization of a closed circular plasmid (ds-DNA) onto the functionalized solid support surface of, e.g., the microarray. This is achieved by using one or several short ss-oligonucleotides whose sequences correspond to part(s) of the covalently closed circular ds-DNA, such as a plasmid. The 3'- and 5'-terminal ends are modified, e.g., by being aminated. The modified DNA covalently binds to aldehydes on the functionalized surface. The single or multiple short oligonucleotides form a triplex-DNA, which does not negatively affect the ds-DNA plasmid. This triplex-DNA is stabilized by a substance such as BQQ, or triplex-DNA binding proteins and then a substance such as psoralen is used to produce a irreversible complex e.g., a covalent bond. Another part of the invention is the use of a UV laser (instead of regular UV irradiation), to crosslink the psoralen to the DNA. This allows for less potential damage to ds-DNA. This attachment allow for most of the plasmid to float freely in a solution of interest. Hence, for example, 4 M NaCl, or spermine can induce negative supercoiling and Z-DNA formation within certain sequences of a gene or sequence to be studied. The invention allows for the immobilization of ds-, and multiple-stranded nucleic acids (PCR ds-DNA, gene fragments, genes, oligonucleotides, synthetic polynucleotides, and ds-DNA plasmids) to a pre-activated or functionalized glass, plastic, or other solid surface. Ds-DNA can be covalently immobilized by either one or two tails. For example, a portion of the molecule can be treated to become single stranded, and then be modified such as by amination, to react with the aldehyde groups of the functionalized surface. These moieties are used to anchor the ds-, or multiple-stranded nucleic acids to the functionalized microarray slide. The efficiency of attachment is improved when the modified-DNA and glass surface aldehydes are placed together in a vacuum-chamber, as opposed to at room temperature.

Multiple-anchors can also be employed with triplex-DNA, quadruplex-DNA, pentaplex DNA, or other multiplex-DNA, as well as covalently closed circular ds-DNA. These immobilized nondenatured nucleic acids are firmly bound to the functionalized microarray surface via covalent bonds, and can withstand heat, washing and subsequent staining procedures.

With respect to the characterization of nucleic acid binding proteins, for example, a DNA binding protein is added to the novel microarray, with, e.g. ds-DNA immobilized on a functionalized solid support surface. The protein is allowed to interact with specific sequences or helical conformations such as with immobilized Z-DNA. The protein is then cross-linked to the ds-Z-DNA. This cross-linking can be accomplished by, e.g., UV irradiation of the DNA-protein complex using 8-1 azidoadenine. Antibodies against the protein can be used to visualize the complex such as a standard biotin-(strept)avidin method, or the protein can be directly labeled with a fluorescent tag.

Proteolytic digestion of the immobilized DNA-protein complex can also be performed. This produces data on DNA-binding domains, sequence characterization of the DNA fragments and characterization of the proteolysed complex. This procedure can be applied to triplex-DNA, quadruplex-DNA, pentaplex-DNA and other multiplex DNA as well as to plasmids.

The invention is especially useful, in, e.g., characterization of left-handed molecules, such as Z-DNA. Left-handed Z-DNA is believed to act as a transcriptional enhancer within eukaryotic genes and may therefore regulate gene expression in vivo.

Sequences of alternating purine-pyrimidine bases can adopt a left-handed helical structure (Z-DNA), which was first defined by an atomic resolution x-ray crystallographic analysis for the hexanucleotide pentaphosphate $(dC-dG)_3$. In this conformation, the antiparallel polynucleotide chains are still bonded by Watson-Crick base pairing, but the guanine bases have rotated about the glycosydic bond and have assumed a syn conformation. The base pairs of the CpG sequence are sheared relative to each other, so that the cytosine residues are stacked on each other. The guanine residues are no longer stacked on the planar bases, but instead interact on one side with the O1' atom of the adjacent sugar ring. As a consequence of these features, the base pairs occupy a position at the periphery of the molecule, exposing the C-5 position of cytosine and the N-7 and C-8 of guanine to the exterior of the molecule. In addition, the sugar-phosphate backbone follows a zigzag course rather than a smooth spiral. Left-handed Z-DNA in solution is provided by the synthetic polynucleotide poly[d(G-C)] exposed to high concentrations (>2.5 M) of NaCl. Numerous crystallographic and other studies documented in the art have established the polymorphic nature of the Z-DNA conformations and delineated the numerous factors that can greatly enhance the probability of the B-Z transition: (1) increased ionic strength; (2) decreased water activity; (3) site-specific interactions of cations and anions; (4) increased temperature; (5) increased negative superhelical density; (6) binding of peptides and proteins, including polyamines, antibodies, and core histones; and (7) chemical modification of the DNA primary structure, such as substitution at the C-8 position of G, placement of a positive charge at N-7 of G, alkylation of the 2-amino group of G, methyl or bromine substitution at C-5 of C, and phosphorothioate substitutions in the sugar-phosphate backbone. Most of the above conditions act synergistically. The conditions under which some of them can adopt the Z form are known. The midpoint of the B-Z transition is 2.5 M NaCl for poly(dG-dC)@poly(dG-dC), 0.7 M NaCl for poly(dG-$m^5$dC)@poly(dG-$m^5$dC), and 0.2 M NaCl for poly(dG-dC)dien-Pt(0.12. The midpoint for poly(dG-$br^5$dC)@poly(dG-$br^5$dC) (Z-DNA) is in the salt range of 5 mM Tris-HCl-3 M NaCl. Poly(dI-$br^5$dC)@poly(dI-$br^5$dC) can adopt the B or the Z forms, depending on the salt concentration. This are just a few midpoint values which will be extremely useful to the investigator using the novel microarray system to characterize B-DNA to Z-DNA transitions.

In a further embodiment of the invention, it can be used for screening for potentially useful substances that, e.g., cause or lead to deterioration of DNA. The invention is useful in e.g., the screening of drugs and antibodies, as described herein. Disease is sometimes caused by various factors which deteriorate nucleic acid molecules within cells. Ligand interactions can promote or obstruct indirect or direct gene/ligand interactions. An important role in ligand action in physiological systems is that of stereoselective hydrogen bonding between biomolecules and effector drugs. Effector drugs can be directly responsible for interactions of nucleic acid transfer reactions. Ligand interaction is mainly involved at a specific site of the nuclear acid molecule, whenever two potential donor/acceptor partners are united. Water molecules often help mediate hydrogen binding. In these systems, hydrophilic interactions compete with hydrophobic interactions.

Nucleic acids and protein are both amphiphatic macromolecules. Therefore, effectors such as drugs acting as amphiphaties are able to direct nucleic acid and protein folding. The inventions not only allows for ds-DNA or RNA and multiple-stranded nucleic acid-drug interaction analysis, as well as also for analysis of, e.g., DNA-histone/drug complexes. It should be noted that several proteins that can bind to bent DNA significantly influence the number of micronucleus-like structures. In cells of higher organisms, DNA exists in condensed form as a left-handed superhelix wound around cationic histone protein octamers in the repeating nucleosomal arrays that comprise the basic chromatin fiber. The tight DNA package makes intrahelical interactions possible. Generally, changes in the secondary structure can lead to organism annihilation, as well as protection of mechanisms.

DNA/drug binding also has a determinative role in pharmaceutical therapy. Genotype interactions of drugs sometimes result in the increased appearance of micronuclei. Multiple interactions between the drug and parts of the biological molecules are possible, such as intercalation, groove binding, stacking interactions with the bases, and reactions with the backbones. Several drugs can cause long-range interference to ds-DNA and can be the cause of micronucleus-formation intensification. As a biological consequence, cytogenic damage and micronuclei formation are frequently observed during chemotherapy, as examples of the biological consequences theory. Some drugs (e.g., adriamycin) also induce chromosomal aberrations, while others have been found to prevent micronuclei formation.

Current research points to a relationship between supercoiled DNA and inducement of micronuclei. Hence, it is not surprising that chromosomal aberrations and micronuclei formation in cells are of increased interest in the development of new drugs and drug therapies. A new theory in the understanding of drug efficacy is the influence of drugs on secondary DNA structure (e.g., curvature inducement) and the formation or prevention of micronuclei in cells. This seems to be important for the comprehension of structure-function relationships in therapy. Supramolecular assemblies of double strands induced by some drugs may be used as models for investigation.

The invention allows for the characterization of DNA/drug complexes in both a loose (naked nucleic acid) and highly condensed (supercoiled DNA-histone/drug complex) solution environment. Supramolecular assemblies of ds-, and other multiple-stranded nucleic acids induced by drugs can be used via the invention, as models for investigation. The invention allows for the examination of multivalent binding agents on the packaging of ds-, and other multiple stranded nucleic acid molecules into condensed structures.

Double-stranded DNA is the molecular target for a large number of drugs that are used in cancer treatment. Many of these drugs are non-specific targets of cytotoxic agents; however, a new generation of DNA drugs that specifically target DNA-associated processes are being investigated. These drugs are much more specific and hence, more effective therapeutic agents. A large number of antibiotic, anticancer and antiviral drugs manifest their biological effects by interacting reversibly with DNA and RNA. Double-stranded and multiple-stranded nucleic acids represent a major target in drug development strategies which are developed to produce new therapeutic agents for cancer, cataracts, AIDS and many other diseases. In order to develop new drugs or to improve old ones, it is important for the investigator to comprehend the specific molecular biological mechanism that regulates DNA-drug, RNA-drug, and/or nucleic acid-protein/drug complex systems. One must characterize all the elements involved in drug-nucleic acid complex structure, kinetics and thermodynamics. The invention facilitates approaches to these needs. Drugs which can inhibit the reproduction of cancer cells by "turning off genes", or antibodies tagged with a drug that can inhibit a cancer can be characterized by use of the invention. It also allows the investigator the ability to obtain information on nucleic acid-targeted drug design that is useful with anti-sense DNA and RNA technologies. The method reveals where the nucleic acid/nucleic acid probe interactions are taking place, the binding mechanism, and if a permanent bond, hydration changes that accompany DNA binding, the base pairs involved, the helical conformation, and if the drug produces region-specific lesions in DNA. The microarrays permit characterization, for example, of a drug and hence aid to develop a rationale for the prospective design of more effective drugs.

One "flow chart" of how a new drug may be characterized is the following:
1. Local water interactions with DNA-drug complexes. Measuring changes in water associated with specific DNA interactions helps in correlating changes in hydration with the strength and specificity of binding.
2. Drug-nucleic acids dissociation kinetics.
3. Drug-nucleic acid temperature interactions.
4. Drug-nucleic acid pH interactions.
5. Drug-nucleic acid ionic strength interactions.
6. Drug-nucleic acid competition assays.
7. Drug-nucleic acid complex.
8. Drug-nucleic acid binding mechanism.
9. Site(s) of nucleic acid/drug binding.
10. Sites of drug-nucleic acid binding; base pairs.
11. drug-nucleic acid interactions with nucleic acids crosslinked to another nucleic acid factor by UV irradiation.
12. Stabilization of drug-nucleic acid complex.
13. Nucleic acid conformational effect on drug-nucleic acid complex.
14. Methyl groups on nucleic acids.
15. Specific mechanism of cytotoxic drug on nucleic acid.
16. Understand conformational and energetic consequences of drug-DNA complexes.

Further, the microarrays of the invention can be employed to characterize established or novel monoclonal or polyclonal antibodies, and identify those that are useful diagnostically or therapeutically. Therapeutic antibodies can be used to either shut down a gene by interacting with its transcriptional and/or translational machinery, or it can bind to nucleic acids and deliver enzymes, toxins, drug or radiation. Therefore, use of the invention can aid in the production of antibodies as pharmaceuticals. High-affinity monoclonal and/or polyclonal antibodies developed against therapeutic targets can be characterized by analyzing their ability to bind nucleic acids.

Recombinant antibodies and their fragments representing well over 30% of all biological proteins undergoing clinical trials for therapy and diagnosis. The invention is useful, e.g., in characterizing engineered therapeutic antibodies. Antibodies can bind to both right-handed ds-B-DNA and left-handed ds-Z-DNA sequences. Therefore, the production of specific antibodies for ds-B-DNA of specific sequences, and Z-DNA of specific sequences has great potential. Therapeutic anti-DNA-antibodies can be used to turn off bad genes. Z-DNA is believed to act as a transcriptional enhancer, and if a anti-Z-DNA antibody binds to an oncogene's transcriptional machinery, this will shut down its gene expression. Similar approaches can be taken with B-DNA sequences, using anti-B-DNA antibodies.

The ds-nucleic acid (e.g., ds-DNA, ds-RNA, RNA/RNA, DNA/RNA, Z-DNA, B-DNA, parallel nucleic acids) molecules, be they of low or high molecular weight, used in this novel array system are either in the ds-right-handed nucleic acid helical configuration [examples: ds-A-DNA: low humidity solution, ds-B-DNA: high humidity solution, C-DNA, D-DNA, T-DNA, A-RNA, DNA-RNA, RNA-RNA (A' and A-form], or ds-left-handed [examples: Z-RNA or Z-DNA, $Z_1$, $Z_{II}$, and Z-', DNA, Z*-DNA (van de Sande, J. H. et al., EMBO J. 1:115–120, 1982), Z(WC)-DNA (Ansevin, A. T. et al., NAR 18:6119–6126, 1990)] nucleic acid helical conformation. Local conformational variations due to different base pairs in ds-B-DNA can also be analyzed in the same way. Some of these ds-nucleic acids are permanently stabilized into a particular helical conformation via chemical modifications, such as left-handed ds-Z-DNA, permanently stabilized into the left-handed Z-DNA conformation either by bromination (Br), N-acetoxy-N-acetyl-2-aminofluorence (AAF), or chlorodiethylenetriaminoplatinum (II) chloride (dien-pt), and then immobilized onto the solid support functionalized substrate surface for interaction with nucleic acid probes, to be characterized by the investigator.

The following is a discussion of the practice of the invention using right handed DNA. It is one embodiment thereof, and should not be construed as limiting the invention.

Right-handed ds-B-DNA arrays are placed in a biochip reaction chamber, housing a nucleic acid probe in a buffer solution such as 150 mM NaCl solution. This buffer is close to the human physiological range, and maintains the right-handed ds-B-DNA conformation (Sinden, R. R., 1994, DNA Structure, and Function. pp. 1–398. Academic Press, NewYork). Ds-B-DNA micro- and macroarrays can be made up of either native DNA, such as gene fragments, or synthetic polymers such as ds-DNA polynucleotides, oliogonucleotides), normal genes or mutated genes such as double stranded oncogenes.

Exemplary of right-handed ds-B-DNA synthetic polymers are: 1. poly(dA-dT).poly(dA-dT), 2. poly(dI-dC).poly(dI-dC), 3. poly(dG-dC).poly(dG-dC), 4. poly(dA-dU).poly(dA-dU), 5. poly(dA-dC).poly(dG-dT), 6. poly(dG-me$^5$dC).poly(dG-me$^5$dC), 7. poly(dA-br$^5$dU).poly(dA-br$^5$dU), 8. poly(dA-io$^5$dU).poly(dA-io$^5$dU), 9. poly(dI-br$^5$dC).poly(dI-br$^5$dC). The skilled artisan will be aware of many others.

Some known anti-ds-B-DNA antibodies are, such as anti-B-DNA-2C10 monoclonal antibody (MAb), anti-ds-B-DNA (B103) MAb, B11, 4260, 2122 and B14 anti-ds-B-DNA polyclonal antibodies. These and many other antibodies can be used to characterize the immobilize, nondenatured nucleic acids. Once again, a nucleic acid probe such as a ds-B-DNA binding protein can be added first and then an anti-antibody nucleic acid probes. The anti-antibody nucleic acid probes can be identified by either the direct or indirect immunochemical method, using an antibody labeled, e.g., with a PAP, a biotin-(strept)avidin system or immunoflourescence.

Similarly, the invention can be used with left-handed Z-DNA. Factors such as DNA supercoiling, high salt concentration, spermine, relative humidity, cross-linking, 3–4 M NaCl concentration (Hasan, R. et al., Biochem. Inter. 20:1077–1088, 1990), Z-DNA binding proteins, anti-Z-DNA antibodies (Lafer, E. M., et al., EMBO J. 4:3655–3660, 1985), polyarginine, as well as other factors, drive the well known B-DNA to Z-DNA transition (Sanger, W., Ed., Principles of Nucleic Acid Structure, Chapter 12, pp. 283–297, 1984, Springer-Verlag, NewYork; Saenger, W., Ed., Principles of Nucleic Acid Structure, Chapter 12, pp. 220–241, 1984, Springer-Verlag, NewYork; Dickerson, R. E., Science, 216:475–485, 1982; Blaho, J. A., Prog. Nucleic Acid Res. Mol. Biol. 37:107–126, 1989; Herbert, A. J., Biol. Chem. 271(20):11595–11598, 1996). Chemical modifications such as modifications caused by bromine, AAF, or chloro (diethylenetriamine) platinum(II) chloride can permanently stabilize the Z-DNA conformation. Dinuclear bis(platinum) complexes induces B6Z transitions in synthetic polymers (NAR 7: 1697–1703). Hydralazine causes B-to Z-DNA transitions in poly(dG-m$^5$dC). MnCl$_2$ at submillimolar concentrations, i.e., physiological range, induces B6 to Z-DNA formation in poly[d(G-C)]. Negative superhelical energies needed to drive the B- to Z-transition at physiological ionic strengths are well within the level of supercoiling found in DNA from cells. The level of negative supercoiling required to form Z-DNA is a function of length. In general, the longer the Z-DNA forming sequence, the less negative supercoiling is needed to drive the B- to Z-transition, which is important in the invention. Z-DNA is very stable in supercoiled DNA, since the formation of Z-DNA effectively unwinds DNA, resulting in the relaxation of supercoils. Z-DNA is a high energy form of DNA and therefore not as stable as B-DNA. It is extremely light sensitive, unlike B-DNA, and therefore the solid phase used cannot be transparent, when using it. This invention helps understanding of how the Z-DNA conformation exerts an effect upon its non-Z-DNA neighbors and B/Z-DNA junctions and the effect of Z-DNA on nucleosome placement.

Not only can B-to Z-DNA conformations be analyzed, but also helical transitions of Z-DNA back to B-DNA. The reversal of the Z-to B-DNA conformation of a synthetic ds-DNA polymer, such as poly(dA-dT).poly(dA-dT) is known to be inducible by drugs, such as netropsin or distamycin A (J. Biomol. Struc. & Dyna. 13: 671, 1996). Hence, compounds of interest can be screened to determine if they mediate this transaction by accelerating it as impeding it. Enzymatic studies can also be performed using this array. General enzymatic binding properties of RNA polymerase II on template conformation can be studied such as the transition from B-DNA to Z-DNA (Eur. J. Biochem. 206: 49–58, 1992).

Left-handed ds-Z-DNA arrays are placed into either a 3 or 4 M NaCl solution, a 0.7 M MgCl$_2$ solution, an alcohol solution, 20 mM sodium citrate (pH 7.2/1 mM EDTA/3.5 M NaCl), 110 mM NiCl$_2$-5.0 M NaCl (0.01M Tris-HCL pH. 4), or other ionic solutions, which keeps a large percentage of ds-DNA in the left-handed Z-DNA conformation. Additionally, ds-Z-DNA microarrays may be placed into a solution of 1 mM LiCl, a solution which is close to the human physiological range. This maintains a large percentage of the ds-DNA in the Z-DNA conformation. On the other hand, Br-ds-Z-DNA is permanently stabilized into the left-handed ds-DNA conformation, while un-Br-ds-Z-DNA is not permanently stabilized and may therefore allow for some fluctuations of ds-B-DNA to ds-Z-DNA back to ds-B-DNA helical conformations. Synthetic DNA polymers (about 100% of this type of immobilized DNA) and native ds-DNA (ds-Z-DNA in genes makes up about 42% to 62% of the total sequences) can be permanently stabilized into Z-DNA by bromination. Ds-Z-DNA micro- or macroarrays can also be made up of either synthetic, nondenatured polymers, normal genes or mutated genes. By employing either monovalent and/or divalent cations, one can convert ds-B-DNA to ds-Z-DNA. Z-DNA can be observed in the synthetic polymer poly(dG-dC).poly(dG-dC) at 3M NaCl (Lafer, E. M. et al., Proc. Natl. Acad. Sci. USA 78:3546–3550, 1981). High concentrations of monovalent cations (example: Na$^+$, K$^+$, Rb$^+$, Cs$^+$, Li$^+$) shield the negative charges and thus stabilize the left-handed Z-DNA configuration. Lower concentrations of divalent cations such as Mg$^{2+}$, Mn$^{2+}$, Co$^{2+}$ are needed to shield negative charges than monovalent cations, and stabilize the left-handed ds-Z-DNA conformation. For example left-handed Z-DNA can be stabilized at millimolar concentrations, physiological range, with cobalt hexamine chloride. As bromintation of these molecules is extremely useful, an exemplary procedure is presented herein; however, it is not to be construed as limiting the invention. A standard approach for brominating Z-DNA follows. It should be understood that others are possible.

1. Dissolve 100 A$_{260}$ units of poly(dG-dC).poly(dG-dC) in 1 ml of ultrapure H$_2$O (ice bath). Low light in the laboratory. Only ultrapure molecular biological grade reagents should be used.
2. Remove 50 A$_{260}$ units and add 5 M NaCl to a final concentration of 3.8 M. The volume at this point should be about 4 ml for convenience in later procedures. Heat to 600° C. in the dark for 10 min for full conversion from B-DNA to the Z-DNA conformation.
3. Dilute 0.1 ml of a saturated solution of Br$_2$ in water (shake extremely well to ensure saturation: Five to ten min) to 2 ml with ultrapure water (final concentration, 11 mM). All procedures with bromine should be performed in a fume hood, with very low light.
4. Add 1/11 volume of 0.22 M sodium citrate (pH 7.2) to the DNA solution (the pH is critical, since it will drop to about 6.4 on addition of salt and bromine). Low light in the laboratory is critical.
5. Add 1/11 volume of the 5% saturated bromine water, and incubate at room temperature for 3 minutes in total darkness. Immediately bubble a gentle stream of air through the Z-DNA solution for 5 minutes using a 2-inch syringe needle to remove the brominated molecules.
6. Dilute 30 μl to 550 μl with ultrapure water and determine the A$_{295}$/A$_{260}$ ratio (spectrophotometrically). A CD spectrum can also be employed.
7. For right-handed ds-B-DNA the A$_{295}$/A$_{260}$ ratio in low salt (150 mM NaCl) is about 0.12. For ds-DNA to be in the Z-DNA conformation, the ratio must be at least 0.3 (0.33–0.38). If the ratio is too low, repeat Steps 5 and 6, reducing the incubation time (the A$_{260}$ drops by about 30% on bromination, therefore, to convert A$_{260}$ to DNA concentration, multiply it by 65 μg/ml. Over a period of time, especially in the presence of light, the left-handed Z-DNA will gradually depurinate, and the A$_{295}$/A$_{260}$ ratio can increase to as high as 0.6).

8. Finally, dialyze the Z-DNA overnight (24 hrs) against 10 mM Tris, 1 mM EDTA, 50 mM NaCl, in refrigerator in total darkness. A final $A_{295}/A_{260}$ ratio of 0.33–0.36 is fine.

Within any genome, less than 0.01% of the DNA is in the left-handed Z-DNA conformation. In human genes, about 42% to 62% (Schroth, G. P. et al., J. Biol. Chem. 267:11846–11855, 1992) of the sequences are in the left-handed Z-DNA conformation. The Z-DNA micro- and macroarrays allow for the identification of potential left-handed ds-Z-DNA sequences, within the ds-B-DNA genes. The method permits specific examination of bases, such as guanine residues of Z-form DNA by different probes, such as antibiotics (bleomycin-nickel (III) (BBA 1308:169–176, 1996, Guan, L. L.).

Some permanently stabilized, ds-Z-DNA molecules are Br-poly(dG-dC).poly(dG-dC); AAF-poly(dG-dC_.poly(dG-dC); poly(dG-5BrdC).poly(dG-5BRDC); poly(dG-5-medC).poly(dG-5medC); dient-poly(dG-dC).poly(dG-dC); poly(dA-dC).poly(dT-dG); halogenated poly(dI-dBR⁵U); Cobalt hexamine $[Co)NH_3)_6^{3+}]$poly(dG-dC).poly(dG-dC). Others are also known.

Many different synthetic ds-B-DNA polymers can be converted to the left-handed Z-DNA conformation, but not permanently, using bromine or other materials; however it should be noted that these non-brominated, and hence not permanently stabilized Z-DNAs may have some Z-DNA to B-DNA fluctuations. The first molecule listed, i.e., poly(dG-dC).poly(dG-dC) can be maintained in the Z-DNA conformation using a variety of different solutions, including those which follow. Alternating purine-pyrimidine sequences, like $(G-C)_n$ easily form Z-DNA.

a. 4M CsCl.
b. 4M LiCl.
c. 6M LiCl.
d. 2.5 M NaCl midpoint conformational change.
e. 0.7 M $MgCl_2$ midpoint conformation change.
f. 4 M NaCl (3 M NaCl).
g. mM concentrations for $MgCl_2+45°$ C. and then cool and remain in Z-DNA.
h. LiCl+elevated temperature.
i. 0.4 mM $MgCl_2+10\%$ EtOH.
j. 4M LiCl at 68° C.
k. ethanolic solutions.
l. methylation.
m. 4 mM $MgCl_2+10-20\%$ ETOH.
n. Zinc.
o. protonation of biopolymers.
p. A novel Z-DNA stabilizing solution.

The second molecule forms Z-DNA, but require greater stabilization energy for their formation than $(GC)_n$, and cannot be stored. A solution of, e.g., 10 mM $NiCl_2+0.2M$ NaCl is good for stabilizing the Z-DNA conformation. In the case of poly (dT.dG).poly B- to Z-DNA developing solutions that are useful include: 4.8M NaCl+20% ETOH, 40 mM$Ni^{2+}$+4M NaCl, ZnN4 and 100 μm Zn. This DNA sequence is difficult, but not impossible to convert B-to Z-DNA. Plasmids, such as PRW 751, which contains 20 left-handed helical sites can be immobilized to the substrate surface, as can molecules such as the negatively supercoiled SV40 genome (DNA minicircle) plasmid. This plasmid contains several sites capable of adopting the Z-DNA conformation in the enhancer region and can be immobilized to the substrate surface. Similarly, pBR322 is a negatively charged, supercoiled plasmid, with inserts of alternating CG sequences of 32 bp and 14 bp, that can form Z-DNA. With respect to probes, many antibodies to Z-DNA are known, including C44, C11, Z22, Z44, MAb, and G4e1, 4255 IgG, goat #10 IgG, Ra442, Ra443a, Ra441, 2122 polyclonal antibodies. Many different Z-DNA binding proteins are available, such as Zuotin (EMBO J. 11(10):3787, Zhang, S.) or zeta-crystallin (J. Histochem. Cytochem. 45:1511–1521, 1997).

Knowing the precise parameters of a specific gene region, such as the promoter, the investigator can employ the invention to examine the generation and statistical mechanical modeling of Z-DNA within the promoter region of a gene. One can also examine the influence of negative supercoiling on Z-DNA sequences within, for example, repressor-operator interactions. Additionally, this area of interest within a gene can be characterized in terms of its interaction with other nucleic acid binding elements.

In the case of triple stranded DNA, the arrays are placed into a microarry chamber with the appropriate ionic solution, for examining a specific type of nucleic acid. An example of triplex-DNA is (dA) $(dT)_2$, and an example of triplex-RNA is (rA) $(rU)_2$. Other sequences which can be employed for the development of triplex DNA are poly(I).poly(A).poly(I) (Chandrasekaran, J. Biom. Struc. & Dynamics.17:1035–45,200); and poly(U).poly(A).poly(U) (Chandrasekaran, 17:1023–34,2000), poly(dT).poly(dA).poly(dT) (Chandrasekaran, J. Biom. Struc. & Dynamics 17:1011–22, 2000). Triplex forming oligonucleotides containing 2'-OMe can also be used with the invention. Intramolecular triplex-DNA can form within a single homopurine-.homopyrimidine duplex (ds-) DNA region in supercoiled DNA at low pH such as pH 5 without $Mg^{2+}$. Certain intramolecular triplex DNA structures can also form in supercoiled DNA at neutral pH with $Mg^{2+}$, especially when protonation is not needed. Exemplary are: $(dG)_{30}.(dC)_{30}$, and poly(Pu).poly(Py). Other triple-DNA helices are $d(CT)_n.d(GA)_n$, and $d(GA)_n.d(CT)_n$. Triplex-DNA can be synthesized in situ, i.e., on the chip, directly on the solid support or synthesized externally off the chip and then immobilized onto the functionalized solid support. Synthesis of triplex DNA can be performed as described by McGavin (J. Mol. Biol. 55:293–298; 1971), Sen and Gilbert (Nature 334:364–366; 1988), and Lee J S (J. Biol. Chem. 269:7019–23, 1994; J. Biol. Chem. 269:3615–22, 1994). The molecules can be stabilized with 8-aminoguanine at both neutral and acidic pH (NAR 28:4531–9, 2000). Triplex DNA binding proteins can be characterized (Kiyama, R., Proc. Natl. Acad. Sci. USA 88:10450–10454, 1991) using the microarray procedure of the invention. Other substances can be used to stabilize the triplex DNA, including polyamines, trans-$[Pt(NH3)2]2^+$, and benzo[e]pyridoindole derivatives (Science 256:1681, 1992).

In the case of quadruplex DNA (four-stranded DNA: G-quartet DNA structure) micro- or macroarrays are inserted into a microarray chamber containing a reaction solution for a specific type of immobilized nucleic acid. Studying four-stranded DNA permits the investigator to examine structures at telomeres: $(G_4T_2)_n$ or $(G_4T_4)_n$. Inter- and intramolecular quadruplex-DNA (G4 or tetraplex-DNA) were synthesized as described by Han (Biochemistry 38:6981–6, 1999), Marathias (Biochemistry 38:4355–64, 1999) and Hardin (Biochemistry 36:15428–50, 1997). Quadruplex-DNA can also be synthesized onto the substrate surface or synthesized off the surface and then immobilized onto the substrate surface. Potassium and sodium can stabilize quadruplex-DNA (Marathias, V. M. NAR 28:1969–1977; 2000): d(GGTTGGTGTGGTTGG). Also, with respect to pentaplex-DNA, microarrays are placed in a microarray chamber solution in the dark. A DNA pentaplex incorporating nucleobase quintets in accordance with (Chaput, J. C.

Proc. Natl. Acad. Sci. USA 96: 10614–10619, (1999), was immobilized onto a solid support array. Cesium ions were used to induce the formation of this nucleic acid. Pentaplex molecules can also be synthesized "on chip" or "off chip", and then used to analyze "nucleic acid probes" or the immobilized pentaplex DNA itself.

All of the synthetic nucleic acid polymers and oligomers described herein are soluble in ultra pure molecular biology grade water or dilute buffers at or near pH 7.0. It is sometimes difficult to wet a lyophilized nucleic acids polymer due to gel formation at the surface of the product; however, techniques such as agitation on a vortex mixer is extremely useful in cases where solubilization is difficult. Deoxyguanosine containing polymers often tend to aggregate when their solutions are frozen or when they are lyophilized, presenting a particularly difficult problem when a solution is required. Mild sonication treatment is helpful in these cases. The polymers are generally insoluble in acid, and since laboratory distilled water is often on the acid side, some addition of dilute sodium hydroxide or ammonia solution may be necessary to raise the pH to 7.0 and dissolve the polymer. Ultra-pure molecular grade water should be used. Heating polymer solutions at 40–50° C. for 5–10 minutes is not harmful. If heating is considered undesirable, an alternative method of dissolving difficult deoxypolymers is to make the suspension alkaline and then carefully neutralize the solution after the polymer has dissolved.

In the practice of the invention, it is to be noted that nucleic acid polymers and oligomers are stable for years when stored at freezing temperatures, as neutral lyophilized powders or fibers. Frozen neutral solutions are reasonably stable for short periods (1–4 months) but gradual hydrolysis of internucleotide linkages and of terminal phosphates will inevitable occur. This process is hastened at higher temperatures. Therefore, nucleic acids should be synthesized, placed and used within two or three weeks.

In describing the molecules herein, the polynucleotides and oligonucleotides are described by the unit rather than by weight. "Unit" is defined as that quantity of nucleic acid material which has an absorbance of 1.0 when dissolved in 1 ml and measured in a 1 cm cuvette. Ultraviolet absorbance of polynucleotides and of duplexes is affected by the ionic strength and the temperature of the solution in which they are kept. All measurements described herein are made at 20° C. in 0.1 M sodium chloride, 0.02 M phosphate at pH 7.0. Most nucleic acid products are characterized as units measured at 260 nm, but Poly(dI) and Poly(dG) are measured at 250 nm and Poly(dC) at 270 nm, respectively.

The methods of the invention can also be carried out with the class of molecules referred to as "homopolymers." These are molecules which consist of a single species of 2'-deoxyribonucleotide, bonded by 3',5'-phosphodiester linkages. The nucleic acid polymers can be prepared, e.g., by the enzymic polymerization of pure 2'-deoxyribonucleotide 5'-triphosphates. After deproteinization, they are extensively dialyzed against EDTA, sodium chloride solution, and ultra-pure water to ensure the removal of all low molecular weight material and other contaminants originating from the enzyme reaction and nucleic acid isolation procedures. The final products are lyophilized sodium salts containing from 14-20 absorbancy units per mg. Each polymer is then characterized by ultraviolet spectrophotometry, by buoyant density measurements and by sedimentation measurements.

Some DNA-homopolymers, Poly(dA) for example, can be difficult to dissolve in water or salt solution. If heating the polymer is considered undesirable, an alternative method of dissolving the molecule is to make the suspension alkaline and then carefully neutralize the solution after the nucleic acid polymer has dissolved. The $S_{20}$-w of each polymer normally varies from 4.0 to 12.0, but 6–9 is ideal. Examples of this type of polymers are poly(dA), poly(dC), poly(dG), poly(dI), poly(dT), and poly(dU). Units are measured in 0.1 M NaCl, pH 7.0 at 260 nm for poly(dA), poly(dU) and poly(dT), at 250 nm for poly(dI) and poly(dG), and at 270 nm for poly(dC). All of the above polynucleotides are best stored at −20° C.

An additional class of molecules useful in the invention are DNA/RNA hybrids. Each of these nucleic acid molecules is a double-strand complex consisting of one RNA-homopolymer and one DNA-homopolymer. They can be prepared by dissolving the homopolymers separately in, e.g., 0.2 M sodium chloride, 0.02 M phosphate pH 7.0, and then mixing equimolar quantities of the two solutions (determined by using the appropriate extinction coefficients), followed by heating the mixtures for 5 minutes at 45–50° C. After annealing, the solutions are dialyzed to remove most of the salts, and lyophilized to yield the sodium salts of the complexes. The lyophilized products can be dissolved in a salt solution, such as 0.1 M sodium chloride or a lower concentration of a salt of a divalent ion, if the double-stranded nucleic acid configuration is desired. After dissolving, one heats the solution at 45–50° C. for 5 minutes to anneal the duplex, and to insure double-strand configuration of the nucleic acid.

Examples of this type of synthetic polymers are poly(rA)·poly(dT), poly(rU)·(dA), poly(rG)·poly(dC), poly(rI)·poly(dC), poly(rC)·poly(dI), poly(rCm)·poly(dG), poly(rAm)·poly(dT), and poly(rGm)·poly(dC). Units are measured at 260 nm in 0.1 M NaCl at pH 7.0. All of these solutions are best stored at −20° C.

Yet a further type of molecule useful in the invention are DNA-alternating copolymers. In these molecules, each strand of polymer contains two complementary 2'-deoxyribonucleosides in precise alternating sequence, bound by 3',5'-phosphodiester linkages. These nucleic acid preparations were synthesized using DNA polymerase from *M. luteus* and pure 2'-deoxyribonucleotide 5'-triphosphates, although other synthetic methodologies are possible and will be known to the skilled artisan. Following synthesis, the nucleic acids are lyophilized and contain 14–20 absorbancy units per mg, measured at 260 nm.

If a concentrated, neutral solution (<10 units/ml) of one of these nucleic acid products is prepared in water, the nucleic acid product will be present in the double-stranded configuration. If a dilute solution is prepared in water, the product will almost certainly be present in the single-stranded form. To insure the presence of the double-stranded configuration, solutions should be prepared in salt-buffer mixtures containing at least 0.1 M NaCl or lower concentrations of divalent salts.

Each of the nucleic acid polymers can be characterized by ultraviolet spectrophotometry, by analytical buoyant density measurements and by sedimentation coefficient measurements. All spectral measurements can be made in 0.1 M NaCl buffered at pH 7.0 with 0.02 M phosphate. The observed analytical values for DNA-alternating copolymers are as follows: the $S_{20}$, w of each polymer normally varies from 4.0 to 12.0, but most lots fall in the range of 6–9. As with the other molecules described herein, they are best stored at −20° C.

Examples of this type of polymer are poly(dA-dT)·poly(dA-dT), poly(dI-dC)·poly(dI-dC), poly(dG-dC)·poly(dG-dC), poly(dA-dU)·poly(dA-dU), poly(dA-dC)·poly(dG-dT), poly(dG-me$^5$dC)·poly(dG-me$^5$dC), poly(dA-br$^5$dU)·poly (dA-br$^5$dU), poly(dA-io$^5$dU)·poly(dA-io$^5$dU), and poly(dI-br$^5$dC)·poly(dI-br$^5$dC). Units are measured at 260 nm in 0.1 M NaCl at pH 7.0.

Still a further type of molecule useful in the invention are so-called "DNA-Random copolymers." These are single-strand synthetic polymers prepared from deoxynucleoside triphosphates and terminal addition enzymes. Each nucleic acid polymer contains about equal amounts of two bases which are arranged in a completely random sequence. Apart from their biochemical interest, these nucleic acid polymers may prove useful in the search for base-specific deoxyribonucleases.

Examples of these polymers are poly(dA,dC), poly(dA,dT), poly(dC,dG), poly(dC,dT), and poly(dI,dT). Units are measured at 260 nm in 0.1 M NaCl at pH 7.0. All of the above are stored at −20° C.

DNA-duplexes constitute the next class of molecules to be considered. These nucleic acid products are double-strand complex of two DNA-homopolymers. Poly(dA)·poly(dT) and poly(dI)·poly(dC) are prepared by dissolving the homopolymers separately in 0.1 M sodium chloride, 0.02 M phosphate pH 7.0; mixing equimolar quantities of the two solutions, determined by using the extinction coefficients, and heating the mixtures for 5 minutes at 40° C. for poly(dA)·poly(dT) and 50° C. for poly(dI)·poly(dC). After annealing, the solutions are dialyzed to remove most of the salts, and lyophilized to yield the sodium salts of the complexes. It is desirable to dissolve these nucleic acids in an appropriate salt solution such as 0.1 M sodium chloride or a lower concentration of a divalent ion, if the double strand configuration is desired. This is particularly so in the case of poly(dI)·(dC) which is the least stable of the common duplexes. After dissolving, the solution should be heated to the temperature mentioned supra to anneal the nucleic acid duplex product. Poly(dG)·poly(dC) is an enzymically synthesized duplex nucleic acid prepared by the method of Litman, R. M. [J. Mol. Biol. 61:1 (1969)] to insure equal incorporation of dG and dC.

Poly(dG)·poly(dC) tends to aggregate and can be particularly difficult to dissolve when in that condition. This nucleic acid duplex can be lyophilized from a 0.05 M sodium chloride solution. Consequently, the A$_{260}$ units/mg for this polymer is in the 8-10 range compared to 15–20 units/mg for the other nucleic acid duplexes products. Each double-strand polymer is characterized by ultraviolet spectrophotometry and, where appropriate, by buoyant density measurements and by sedimentation measurements. Polymers are stored at −20° C.

Examples of this class of polymer include poly(dA)·poly(dT), poly(dI)·poly(dC), poly(dG)·poly(dC), poly(dA)·poly(dU). Units are measured at 260 nm in 0.1 M NaCl at pH 7.0.

Oligothimidylates make-up two complete series of molecules, ranging from oligo(dT)$_2$ to oligo(dT)$_{20}$. They are prepared by known methods and are isolated as sodium salts after separation by, e.g., Sephadex A-25 chromatography. The homologous nature of these nucleic acids are clearly revealed by paper chromatography in n-propanol/concentrated NH$_4$OH/H$_2$O:55/10/35(v/v). The oligodeoxythymidylic acids, e.g., oligo(dT)n, are all lyophilized in the form of sodium salts and contain approximately 20 absorbancy units per milligram at 260 nm.

Yet a further class of useful compounds are molecules with dephosphorylated oligodeoxythymidylates, i.e., molecules with no 5'-terminal phosphate. These can be prepared from the corresponding oligonucleotides containing a 5'-phosphate by treatment, e.g., with alkaline phosphatase. Following elimination of the phosphatase with alkali, the oligomers may be further purified by ion-exchange chromatography. Additionally, oligodeoxycytidylates, oligodeoxyguanylates and oligodeoxyadenylates can be used as immobilized nucleic acids. Exemplary of this type of polymers are oligo(dT)30, oligo(dA)2-60, oligo(dC)2-60, and oligo(dG) 2-60.

Finally, other DNA-oligonucleotides which can be used are deoxydinucleotides, deoxydinucleoside monophosphates, deoxytrinucleotides, oligodeoxynucleotides, mixtures of self-complementary oligomers, and non-complementary oligomers with alternating base sequence. Units are measured at 260 nm in 0.1 M NaCl at pH 7.0. All of the above are stored at −20° C.

Polyribonucleotides are yet another type of molecule included in the invention. Double strand Poly(I)·Poly(C) can be prepared by combining equimolar quantities of polyinosinic acid and polycytidylic acid, dissolved in a suitable buffered saline solution. To insure the purity of the double stranded polymer, only the highest purity polyinosinic acid and polycytidylic acid should be used. Formation of double strand polymer can be observed via a large hypochromic effect and then can be confirmed by ultracentrifuge determinations. Double stranded Poly(I)·Poly(C) tends to dissociate into homopolymers in the absence of salt, and thus should be used in a buffered salt solution of sufficient ionic strength to retain the double stranded configuration. Other polydeoxnucleotides which can be used include poly(A)·poly(U) (Michelson. Progress in Nucleic Acid Res. & Mol. Biol. 6: 107; 1967). Other polyribonucleotides include random copolymers, and single-stranded polynucleotides, such as poly(A,C), poly(A,G), poly(A,I), poly(A,U), poly(C,I), poly(C,U), poly(I,G), poly(U,G), and poly(U,I).

The solubility of polyribonucleotides depends on the ease of wetting the polymer. Agitation with a vortex mixer is helpful. When water is the solvent, the pH of the solution should be considered, because polyribonucleotides are insoluble in acid conditions and are degraded by alkali. These polymers are not harmed by heating to 40–50° C. for several minutes at neutral pH. When sterile solutions of double strand polynucleotides are required, it is best to sterile-filter the individual homopolymers and then mix and anneal as described supra. This avoids the losses and problems that occur when trying to sterile-filter viscous solutions of double strand polymers. Best results are obtained when polymer concentrations are low (1 mg/ml or less). In general, polynucleotide solutions at pH 7.0 are stable for several days at refrigerator temperatures and for several months at freezer temperatures. Each preparation should undergo very extensive treatment for protein removal—at least five phenol extractions.

The following examples describe some of the ways one can use the processes of the invention; however, the invention should not be viewed as being limited to these specific embodiments.

EXAMPLE 1

This example describes how to immobilize multistranded, and circular nucleic acid molecules on nylon members. Ds-DNA (and RNA) bind equally well to either nylon membranes or nitrocellulose filters; however, triplex, quadruplex and pentaplex-DNA bind much better to nylon membranes. Additionally, the nitrocellulose filters are fragile and the intact, nondenatured nucleic acids bind non-covalently [nucleic acid binding is 75–110 μg (cm$^2$)]. Nucleic acid binding with the nylon membranes is 470–610 μg nucleic acid/cm$^2$. The nitrocellulose filters only bind nucleic acids in high ionic strength solutions, which prevents examination, for example, of right-handed ds-B-DNA in low ionic salt solutions. Nylon membranes bind nucleic acids at either low ionic strength solutions, such as B-DNA in 150 mM NaCl or high ionic strengths, such as Z-DNA in a 4 M NaCl solution. Therefore, they are superior solid support systems for the novel microarrays of the invention. Nylon membranes can cross-link nucleic acids to their surfaces, forming covalent bonds. Such bonds are very difficult to break and so the nucleic acids are essentially permanently linked to such membrane. Crosslinking occurs via UV treatment and/or drying. The invention allows for high binding capacity and low background noise, with nonfluorescent detection systems. The simultaneous use of vacuum, baking and UV irradiation procedure allows for optimal immobilization, especially for immobilizing multiple-helical nucleic acids to the nylon membrane. The immobilization can be accomplished using the following protocol.

1. All nondenatured nucleic acids and nucleic acid-factor complexes (e.g., nucleic acid protein complexes) were kept at −20° C. and were allowed to warm to room temperature before sample preparation.

Samples of nucleic acid-factor complexes should be prepared in neutral saline.

Just prior to immobilization, all nucleic acid conformations should be characterized via UV-absorption spectra and/or circular dichroism spectra.

Differential scanning calorimeter measurements should be made for DNA-drug complexes prior to immobilization in the range of 20–90° C., with heating and cooling ranges of about 6° C./min.

All procedures must be performed in a clean room environment.

Either nylon membranes with a net neutral charge or a positive charge can be used. This choice of membrane must be made in accordance with the properties of the molecules to be immobilized, such as helical confirmation number of base pairs, and molecular weight. Hybond N is a particularly preferred embodiment.

Microarray Slide preparation:
   a. Wet surface with ultra-pure $H_2O$, for 15 min at 50° C.
   b. Remove $H_2O$: aspirate.
   c. Immediately add nucleic acids in their appropriate transfer buffer, i.e.:

1) Double-stranded (Ds-) DNA: 10×SSC (Fords-DNA, membranes with <0.2 μm pore size allow for the best retention efficiency).
2) The nylon membrane can support nucleic acid sequences of about 340 bp or less.
3) For triplex-DNA, quadruplex-DNA and pentaplex-DNAs, >0.2 μm pore size, may be used, 0.2 μm pores are preferred.
4) For nondenatured ds-, and multiple-stranded nucleic acids less than 480 bp, the 10×SSC should be substituted with 20×SSC nucleic acid transfer buffer: 3.0 M NaCl, 0.3 M sodium citrate, pH 7.0.

Non-Brominated (Br-) left-handed ds-Z-DNA should be placed into a solution of, for example, 4M NaCl.

6) Left-handed ds-Br-Z-DNA should be placed in a solution of, for example, 150 mM NaCl.
7) Right-handed ds-B-DNA should be placed into a solution of, for example, 150 mM NaCl.
8) Right-handed ds-A-RNA should be placed into a solution of, for example, 150 mM NaCl.
9) Left-handed ds-Z-RNA should be placed into a solution of, for example, 4 M NaCl.
10) Triplex-DNA should be placed into a solution of low pH, which depends on bp composition.
11) Quadruple-DNA should be placed into a solution with a high $K^+$ solution, which varies depending on length.

Nucleic acids should be spotted, i.e., arrayed directly onto the microarray surface, using an established protocol from a robotic or manual arraying device.

Nucleic acids need to remain on the solid support for about 5 hours, under vacuum conditions, to be properly immobilized. Nucleic acids should be arrayed from a source plate concentration of 250–420 μg/ml in appropriate buffer as noted, supra. Arraying onto a wet slide can cause the spotted nucleic acids to diffuse.

Nucleic Acid Immobilization Procedure:
a) To permanently immobilize the nucleic acid on the nylon membrane via covalent bond formation three steps are used. These can be carried out sequentially, or, more preferably, simultaneously: vacuum, baking (65–80° C.) and laser UV light source, or standard UV irradiation (254–330 nm for 2–6 min, 22 cm away from the source). The total exposure must be 120 $mJ/cm^2$ for damp nylon membranes. Laser UV light is preferred.

b) Nylon membranes can also be dried in an environmental control chamber, such as a vacuum at room temperature, before using them with nucleic acid probes (example: ds-DNA binding protein). Drying in a vacuum oven can also be performed, e.g., at 80° C. for 2 hr.

c) The baking and UV irradiation steps can also be used separately.

d) Microwave Irradiation can also be employed for 2–4 min at, e.g., 750–900 W, by itself or in combination with the above mentioned immobilization steps.

Nucleic acids should be dispensed onto a 400 μm spot.

Microdeposition is preferred over "in situ" synthesis.

Nucleic acid concentration should be about 100 ng/ul (corresponding to 100 pg/spot for a 1-nl deposition). Volume deposited per spot can range from 10 pL to 10 nL.

All samples should be spotted in triplicate for higher data confidence.

Prior to deposition of the various ds-, and multiple-stranded nucleic acids, a blocking solution may be used. Exemplary is Denhardt's Reagent—1×(0.2% Ficoll, 0.2% polyvinylpyrrolidone, 0.02% bovine serum albumin). Dry the slides, and store them in a dust-free environment (−200C).

Following the immobilization, the nucleic acids are contacted with a labeled probe.

Exemplary of such probes are proteins, antibodies, or other probes described infra. Many different methods can be used to label the probes: For proteins see Giesen, A. W., 2002, Journal of Bimolecular NMR. 22(1): pages 21–62; drugs such as fluorescent phosphoinositide derivatives can be used [Tuominen, E. K. 1992, European Journal of Biochemistry. 263(1): 85–92].Nucleic acid probes can be either directly or indirectly labeled.

1. A microarray spotter can be used to deposit the probes. For example, one may pipette an appropriate amount of nucleic acid probe and then incubate the mix at 4° C. in the dark for from 5 to 12 hours, or overnight.
2. The solution is then aspirated, and the arrays can be washed, e.g., three times, with PBS-BSA-Tween solution for 3 min at room temperature.
3. If needed or desirable, one may block the remaining sites on microarray slide with PBS-BSA solution at room temperature for 1 hour.

Following additional washing, the protocol used will vary, depending upon the probe that is used. For example, if an alkaline phosphatase conjugated antibody is used, one prepares doubling dilutions of antibody in PBS-BSA from 1/50 and adds 200 µl of each dilution in duplicate to separate wells. These are incubated at room temperature for 2 hours, followed by three washes. One then prepares a 1/500 dilution of alkaline phosphatase conjugated anti-immunoglobulin in PBS-Tween and add 200 µl of this to each well. This is incubated at room temperature for 2 hours followed by 3 washes. Then, one adds 200 µl p-nitrophenyl phosphate solution to each well and incubates at room temperature for 30 min. Then 50 µl 3 M sodium hydroxide is added to each spot (400 microns), mixed, the absorbance of each well at 400 nm is read in the spectrophotometer, microelisa reader, or microarrayer scanner.

In the case of chiral metal DNA probes, one uses approximately 50 µM DNA-nucleotide with 3 µM $Co(DIP)_3^{3+}$. Ratios may vary and the reaction will still be efficient. Typically, one irradiates a 20 µl solution at 315 nm for 90 seconds. Racemic $Co(DIP)_3^{3+}$ can be used to determine optimal conditions. The nicking reaction will be directly comparable to that of the enantiomers.

The final $Co(DIP)_3^{3+}$ concentrations should not be higher than 10 µM in buffer, since solubility is low in aqueous media.

A buffer may be used, such as 20 mM Tris-acetate, 18 mM NaCl, pH 7.2. The ionic strength of the buffer (both cationic and anionic, i.e. EDTA) will affect the binding of $Co(DIP)_3^{3+}$ to DNA, and should be kept fairly low. pH will affect the efficiency of the nicking reaction.

With respect to the laser being used, an He/Cd laser at 325 nm, or an Hg/Xe lamp (1000 W, 315±10 nm) are preferred examples. The final power of both of these are larger than 9 nW and irradiation for 90 seconds produces about 50% nicking.

If DNA binding proteins are used, the methodologies of, e.g., Gagna, et al., 64:379–391 (2001), incorporated by reference, may be used.

Detection of binding can be, e.g., chromogenic, fluorescent, radiolabeled, or chemlumiminescent [Kerr, M. A., and Thorpe, R. (Ed.). Immunochemistry: Lab Fax. BIOS Scientific Publishers, Academic Press, pp. 1–256]. Both direct or indirect detection methods can be employed. Enzyme-conjugated antibodies can be employed, as can radiolabeled antibodies.

Determination of binding is carried out, using, e.g., a microarray scanner and a microarray data management program. The artisan will be aware of various options in these areas, and will choose the appropriate ones, depending upon the type of labeling system used.

EXAMPLE 2

By sanding glass, or plastic slides, these slides become 3-dimensional solid support surfaces for high nucleic acid binding capacity. The surfaces can also be functionalized by precoating with substances such as poly-L-lysine or may be UV irradiated for the plastic microarray slides.

The slides should must be precleaned with, e.g., 95% molecular biology grade ethanol, and all procedures must be performed wearing gloves under a laminar flow hood.

The surface is scraped or sanded, preferably with sandpaper.

The sanding is carried out in several stages, starting with very fine materials prior to treatment with coarser ones. Excess glass and sandpaper residue is the removed, and the surfaces are washed in warm PBS buffer, 20 times. If glass is used, the materials should be washed in acid solution for 13 hours and rinsed overnight in running dd-d $H_2O$.

Plastic slides need not be "acid washed".

EXAMPLE 3

In this preferred embodiment, surfaces are functionalized using ultraviolet light. To avoid the use of DNA-protein conjugates such as poly-L-lysine as a coating antigen, which may alter the helical conformation of the immobilized molecule, a polystyrene plastic microarray system was developed to immobilize ds-, and multiple-stranded nucleic acids, using ultraviolet laser light. All procedures must be performed in a clean room environment. Using polystyrene plastic slides as a model, these are washed in a mild detergent, and rinsed overnight with ultrapure molecular biological grade $H_2O$. Plastic slides are dried at room temperature, and labeled for future recognition. They are then irradiated with a U.V. light source such as a germicidal lamp, at 120 µW at 1 m. The distance should be about 70 cm. U.V. irradiation should continue overnight or for about 15 hours. The microarray surface is now functionalized and is ready for treatment with the molecules of interest.

Immobilization of the molecules onto the functionalized surface takes about 2.5 hr (for ds-DNA), and about 3–4 hr (for other multistranded molecules).

The slides must be washed with, e.g., TBS, five times, 3 minutes each wash, in a low light environment.

Control slides can be prepared which, e.g., consist of no immobilized nucleic acids and/or no UV irradiation. The U.V. light treated microarray slides will retain ss-DNA and ds-B-DNA for 7 to 10 days if stored at 4° C., or 10–20 days at 4° C., in a slide box and vacuum sealed for B-DNA, or 6 to 9 days if in dark, at 4° C. for Z-DNA, or for 4 to 6 days, if at 4° C. and light is constantly on.

Both B-DNA and Z-DNA reactivity remain for several weeks at −20° C., even longer if vacuum sealed, without light.

UV light does not denature ds-DNA to the ss-DNA state, as tested by anti-ss-DNA Abs.

This method is preferred for preparing the slides, because the use of poly-L-lysine can be extremely difficult, tedious and, if not done properly, produces negative results. UV pretreatment of polystyrene in the presence of air molecules is believed to be associated with ring opening oxidation, as well as with the formation of chemically reactive muconic dialdehyde structures (Rabek, 1985 in Singlet 02. Vol.14 Polymers & Biomolecules, ed. AA Frimer CRC Press. Boca Raton, Fla. pp. 16.). If the technique is applied with the novel sanded surface technique of Example 2, the 3-dimensional surface allows for even more enhanced immobilization.

EXAMPLE 4

This novel nondenatured microarray described supra immobilizes intact nondenatured nucleic acids to the functionalized surface of the microarray. Therefore, the nucleic acid of interest is "free-floating", as it is anchored by one or more single-stranded arms, which can be formed by, e.g., primer DNA sequences, or formed by ExoIII exonuclease digestion. Many different functionalized microarray surfaces can be employed, along with many different anchoring mechanisms on the ss-DNA tail. What following is a non-limiting list of different functionalized surface solid supports along with the specific anchoring elements attached to the single-stranded modified DNA tail: biotin-labeled DNA/ streptavidin functionalized surface, thiophosphorylated-DNA/poly-L-lysine functionalized surface, carboxylated-DNA/aminated functionalized surface, phosphorylated-DNA/aminated functionalized surface, aminated-DNA/ isothiocyanate functionalized surface, aminated-DNA/ aldehyde functionalized surface, aminated-DNA/epoxide functionalized surface, aminated-DNA/carboxylic acid functionalized surface, aminated-DNA/phosphorylated functionalized support, thiol-modified DNA/3-mercoptopropyl-silane functionalized surface, disulfide-modified DNA/mercaptosilane functionalized surface, disulfied-modified-DNA/amino silane functionalized surface (via a heterobifunctional crosslinker), thiol-modified DNA/amino silane functionalized surface (via a herterobifunctional crosslinker), and 5'-terminal acrylamide modified DNA/acrylamide monomer functionalized surface. At least 14 different methods can be employed to anchor various types of nucleic acids molecules, including, but not being limited to: ds-DNA (RNA), triplex-DNA, quadruplex-DNA, pentaplex-DNA, quadruplex-DNA and covalently closed circular ds-DNA plasmids. Therefore, at least fourteen different standard immobilization procedures, can be used to anchor at least different helical forms of nucleic acid molecules. Attaching modified nucleic acids to activated glass surfaces allows the investigator the ability to characterize nucleic acid/probe interactions.

All the immobilized nucleic acids must have one (or more) tails so they can be anchored to the functionalized glass surface of the microarray. If a restriction endonuclease such as ExoIII is used to prepare the tail, then the nucleic acid molecules must have the opposite end of the intact nondenatured nucleic acids protected from digestion. Therefore, this opposite end must be capped using, e.g. for ds-DNA, alpha-phosphorothioate dNTPs at the 3' end. Triplex-DNA, quadruplex-DNA and pentaplex-DNA should have their ends covered by 3, 4 and 5 alpha-phosphorothioate dNTPs, respectively.

Depending on the specific type of immobilized nucleic acid, its base pair composition, its length and/or molecular weight, its interaction with other substances, and its helical conformation, the investigator must consider temperature, humidity, and other factors in the anchoring.

When double-stranded nucleic acid molecules are used, there can be anchored to the functionalized surface of the microarray slide, by either one tail 5'-terminal, e.g., two tails (5'-terminal of one DNA strand and 3'-terminal of the other DNA strand, all at the same end of the DNA molecule, three tails 5'-terminal and 3'-terminal of one DNA strand, at one end of the DNA, and the 5'-terminal of the other strand, at the other end of the ds-DNA, or all four DNA-modified terminal end tails of the ds-DNA can be simultaneously immobilized to the solid support system. Here, with the last two mentioned immobilizing procedures the ds-DNA forms an upside down U shape. For example, the 5'-terminal end of one strand and the 3'-terminal end of the other strand, on the same side of the ds-DNA may be aminated. The 5'-terminal and 3'-terminal phosphate groups of the aminated-DNA form a covalent bond within the 400 μm spotted region of the functionalized solid support which is positively charged with aldehyde groups. This allows for the ds-DNA molecule to float freely, via its double anchors, within the solution of choice. The investigator can now change solutions and/or add nucleic acid factors and/or use competitive binding assays to characterize the various binding properties of the nucleic acid binding probes. Therefore, using ds-DNA RNA, or DNA-RNA hybrids it is possible to immobilize the nucleic acid via 4 different methods, two being free-floating linear ds-DNAs and 2 being free-floating upside down U shaped ds-DNAs.

The same principles discussed supra for ds-DNA apply to multistranded molecules as well. Any of one, two or three terminal ends of one triplex-DNA strand can be modified for anchoring to a functionalized surface. Additionally, either one, two or three more strands from the other end of the helix can be used in many different combinations. These various combinations lead to 3 "free floating" linear triplex-DNAs immobilized only at one end of the triplex-DNA, and 9 "free floating" upside down U shaped triplex-DNAs, where the nucleic acid molecules are immobilized at both ends.

Similarly, for quadruplex DNA, one, two, three or four terminal ends of one quadruplex-DNA strand can be modified for anchoring to a functionalized solid support microarray surface. Additionally, either one, two, three or four strands from the other end of the quadruplex-DNA can be used in various combinations leading 25 or more different immobilizing combinations. These various combinations lead to 4 "free floating" linear quadruplex-DNAs (all bound at one end of the quadruplex-DNA), and 16 "free floating" upside down U shaped quadruplex-DNAs (bound at both ends of the molecule).

With respect to pentaplex DNA, one, two, three, four or five terminal ends of one pentaplex-DNA strand can be modified for anchoring to a functionalized solid support surface all at one end of this molecule. Additionally, any of one, two, three, four or five strands from the other end of the pentaplex-DNA can be used in many different combinations to immobilize this other end. These various combinations lead to 5 "free floating" linear pentaplex-DNAs, and 25 "free floating" upside down U shaped pentaplex-DNAs.

EXAMPLE 5

This example describes the immobilization of non-denatures molecule including nucleic acid molecules to a functionalized glass support. A functionalized solid support surface is prepared as described, supra. Immobilization of e.g., aminated ds-, or multiple stranded DNA to a glass solid support functionalized with aldehydes is preferred, forming a covalent bond with all the different types of nucleic acid molecules.

Additionally, this process does not need any coupling agent.

Other modified-DNA tails can also be used to immobilize the nondenatured nucleic acids, including biotin-labeled DNA with an avidin or streptavidin functionalized surface, and thiophosphorylated-DNA, where poly-L-lysine is used to functionalize the surface, and other materials, as described supra.

Nondenatured nucleic acids are placed onto the functionalized solid support of the microarray slide, using standard methodologies, such as with a 0.2-mm diameter pin-tool. Resulting spots should be 400 μm in diameter. The distance between two adjacent spots should be 600 μm. Volume deposited per spot with this novel microarray system is 50 to 500 pL, but 10 pL to 10 nL is feasible. The diameter of the spots can range from 100 μm to 1,000 μm. The number of spots created with the microarray of the invention range from 200 to 50,000, although 100,000 spots per array is feasible. Both contact-based or noncontact based microarray instruments can be used, as long as the depositing pins do not damage the intact nondenatured nucleic acids. The proper controls should be used to ensure that all the deposited nucleic acids are not damaged.

The nondenatured nucleic acid molecules chosen, to be immobilized onto a solid support surface can include, e.g., ds-DNA (RNA, DNA-RNA hybrids), right-handed ds-B-DNA, left-handed ds-Z-DNA, left-handed Br-ds-Z-DNA (permanently stabilized), triplex-DNA, quadruplex-DNA, pentaplex-DNA, covalently closed circular ds-DNA plasmid, nucleic acid-nucleic acid probe complexes, and, single-stranded DNA, as well as others.

One chooses an appropriate buffer for maintenance of appropriate nondenatured helical conformation of nucleic acid. For example, 150 mM NaCl is used for right-handed ds-B-DNA, and 4M NaCl for left-handed ds-Z-DNA. Arrayed slides should not be used for experiments until they have remained exposed to proper buffer for from about 1 to about 4 hours, depending on the type of immobilized nucleic acid molecules. For nucleic acids permanently stabilized in a specific helical conformation, such as Br-ds-Z-DNA, they can be suspended at a concentration of 0.5 µg/ml in 3×standard saline citrate (SSC). Nucleic acids should be arrayed from a source plate concentration of 250–420 µg/ml in appropriate buffer solutions. The volume of dispensed nondenatured nucleic acids should be 1 nl. Humidity control is critical, since humidity influences helical conformations of nucleic acids. The investigator must choose the appropriate humidity (%) for the specific nondenatured nucleic acid of interest. For example, ds-PCR nucleic acids can be spotted onto slides at 22° C. and 45% relative humidity. If needed, depending on type of immobilized nucleic acid, block remaining binding sites on microarray with PBS-BSA solution at room temperature for 1 hr. This is followed by washing with 2 changes of PBS-BSA-Tween for 3 min at room temperature.

All nucleic acid probes must have a tail of single-stranded DNA added on in order to immobilize the DNA. Multiple tails hold down the immobilized nucleic acids more firmly, especially the triplex-, quadruplex- and pentaplex-DNAs and are preferred with multistranded molecules.

Storage of this microarrays can be performed by first air drying and storing in the dark at 25° C. Air drying can be substituted by using nitrogen steam to remove excess moisture. The characterization of nucleic acid probes (example: drug) can be performed as described elsewhere. Controls can include the omission of nondenatured nucleic acids from the functionalized surface. Additional controls can be used during the staining procedures (example: Biotin-avidin antibody detection. Omit primary antibody).

EXAMPLE 6

The nucleic acid molecules to used in the arrays can be obtained in any of the standard ways for doing so. Native nucleic acids such as genes or gene fragments can be easily obtained via, e.g., phenol-chloroform extraction and then purified by standard molecular biological methods. Synthetic polymers can be purchased commercially, and can be synthesized, cloned, or modified with single-stranded primers. A primer of ss-DNA, can be attached to the 5'- or 3'-end of a ds-DNA or a multiple-stranded nucleic acid. Another method is to use the ExoIII exonuclease digestion system (Henikoff, S. Gene 28:351) which is commercially available. The nucleic acid of interest should have some added base-pairs at both ends, such as 25–30 extra base pairs. This can be easily accomplished by any of many different methods known to the artisan. These added nucleic acid bases allow for tail development via, e.g., ExoIII base digestion and for the addition of alpha-phosphorothioate dNTPs. Bases can be "chewed off" to make the ss-DNA tail as long as is needed. The extent of base removal for the tail is determined by the artisan. Exonuclease III (Exo III) digestion is used to specifically remove DNA from a 5'-protruding or blunt end restriction site. A specific restriction endonuclease can be chosen to create a "sticky end" so that the ExoIII can perform its function. The adjacent sequencing primer binding site is protected from ExoIII digestion by a 4-base 3'-overhang restriction site or by an alpha-phosphorothioate-filled end. The steady (uniform) rate of digestion allows removals of predetermined lengths from a 5' protruding or blunt end restriction site to be made by removing timed aliquots from the reaction. The bases can be "chewed back" on the 3' prime to 5' prime of the ds-DNA, to any desired length, without involving the nucleic acid sequences of interest. The ss-DNA tail can then be modified as described supra for immobilization to the functionalized solid support surface.

EXAMPLE 7

The example describes a method for immobilizing circular DNA, such as plasmids, to a solid support. A method has been developed to firmly immobilize covalently closed, circular ds-DNA plasmids, which may or may not include gene or gene fragment inserts, or ds-DNA plasmids with either inserted triplex-DNA, quadruplex-DNA or pentaplex-DNA sequences placed into the middle of the ds-DNA plasmids. Any of the above referenced nucleic acid molecules can have specific factors covalently bound thereto, such as UV crosslinked protein it and then be immobilized to the solid support. This permits examination of the effects of DNA supercoiling be it positive or negative on ds-, and multiple-stranded nucleic acid molecules interactions with nucleic acid factors such as drugs, chemicals, proteins, enzymes, and chiral metal molecular probes.

DNA supercoiling is recognized as a powerful in vivo mechanism which regulates eukaryotic gene expression.

This technique involves attaching either a very short ss-DNA oligonucleotide, such as a 5'-phosphorylated 59 mer a fragmented 59 mer, where and each piece labeled at the 5'- and 3'-ends such as by amination, to a very small part of the ds-DNA plasmid such as at the replication origin of a phage: 18 bp oligopurine-oligopyrimidine, which then forms a non-covalent triplex-DNA helical conformation. This attachment occurs to a non-transcriptional region of the plasmid. All pUC family plasmids can be used, such as pGL3, pEGFPC1 and pGA2. The 5'-phosphorylated oligo winds around the ds-target DNA. This oligonucleotide is labeled such as by biotin, carboxylation, amination, disulfied-modification, or acrylamide modification). These DNA modifications are made at both of the 59 mer 5'-phosphorylated oligonucleotide referred to supra, anchor ends the molecule to the functionalized surface of the to solid support. This methodology anchors large plasmids and allow for characterization of novel drugs using competitive binding assays.

The next step involves the addition of triplex-DNA stabilizing agents including: the polycyclic compound BePI which, strongly stabilizes TG- but not AG-containing triples, and/or BBQ, and/or native triplex-DNA binding proteins. These ligands stabilize the newly formed triple-DNA conformation. The formation of the stabilized triplex-DNA is noncovalent. Next of psoralen is added, which covalently crosslinks the triplex-DNA upon UV laser treatment.

For 5'-phosphorylation, 375 pmol of the 59 mer oligonucleotides were placed into a solution of 55 µl of T4 DNA ligase (10 mM $MgCl_2$, 50 mM Tris-HCl, 10 mM DTT, 1 mM ATP, 25 µg/ml BSA, 26° C. at pH 7.9. To this was added 10 U T4 PNK for 95 min at 37° C. In order to produce the union of the ds-DNA plasmid and the 59 mer oligonucleotides, 400 nM of the oligonucleotides was mixed with the plasmid in a buffer containing 200 nM (4.3 µg in 10 µl) plasmid and 10 to 15 µM BQQ (or other triplex stabilizing agent) in T4 DNA ligase buffer. The solution was slowly heated to 77EC (5 min) and slowly cooled to 37EC. Psoralen was then added [Ussery D W, Sinden R R. 1993. Biochemistry 32(24):6206–13] and quick flash UV laser exposure performed [Vedaldi D, Piazza G etc., 1997. Farmaco 52(11):645–52].

EXAMPLE 8

The preceding examples describe methods for immbolizing nucleic acid molecules in accordance with this invention. What follows is an exemplary protocol for immbolizing proteins, such as antibodies, to a solid support. The methodology is applicable to any type of antibody, as well as other types of proteins, including DNA binding proteins such as Zeta crystallin.

A plastic support is sanded, as described supra, using various sand papers, to produce a three-dimensional surface. Following this, the surface is treated with ultraviolet radiation, also as described supra, to activate the surface.

A protein is then addd to the surface. In the case of antibodies, the concentration may vary from, e.g., about 10 to about 100 micrograms/ml in the case of polyclonal antibodies and from about 1 to about 10 micrograms/ml of monclonal antibodies, although these ranges can certainly be extended. In the case of proteins like nucleic acid binding proteins, concentrations can vary, with a preferred concentration being about 50 micrograms/ml.

The protein solution is diluted in an appropirate buffer, such as an immunochemical buffer containing, e.g., 5 mM tris-HCl, pH 7.5, and 50 mM NaCl. The protein solution is micropippetted to the solid support, in the dark, and placed in a vacuum oven with mild heating until the solution evaporates.

Alternatively, one can irradiate the solid support with ultraviolet radiation as described supra, simultaneously with the heating in the vacuum oven. In a third embodiment, the solution can be permitted to evaporate at room temperature.

Regardless of the protocol used, while it should go without saying, it is to be understood that proper laboratory practice dictates that a dust free room be used to immobilize the proteins.

Following the immobilization, the solid supports are washed, three times using PBS-BSA containing 0.05% w/v Tween 20, or other mild buffers at room temperature, and then stored in the dark.

The foregoing disclosure sets forth various features of the invention which include, inter alia, methods for immobilizing molecules such as multistranded nucleic acid molecules, to a solid support. "Multistranded" as used herein, refers to any nucleic acid molecule which consists of two or more strands. Preferably, the molecules consist of 2–10 strands, and more preferably, they consist of 2, 3, 4, 5 or 6 strands. Also a part of multistranded nucleic acid molecules are those molecules where at least one strand is shorter than one or more of the other strands. "Nucleic acid molecule" can refer to DNA, RNA, as well as more complex structures such as pDNA, and other complexes of nucleic acid molecules and other, non-nucleic acid molecules. These nucleic acid molecules may be linear, or circular, such as plasmids, including plasmids which are at least partially supercoiled.

The multistranded nucleic acid molecules may be immobilized to the solid phase in a number of ways. In one embodiment, which results in a so-called "free floating" structure the nucleic acid molecule is immobilized by modifying a part of at least one strand, at one or both ends. Generally, this requires at least part of the molecule to be in "single stranded" form, i.e., in a form where a number of nucleotides in the molecule are not hybridized to others. One can produce such structures in a number of ways, including the use of enzymes, such as exonucleases which essentially "chew" part of one or more strands of a multistranded molecule, resulting in a longer, single stranded portion of one strand, attachment of primers by, e.g., DNA ligases or other means, extension via PCR, and so forth.

Once the appropriate structure is created, it is modified so as to facilitate adhesion to a solid support. The type of modification will vary, depending upon the nature of the solid support. In one embodiment, for example, the single stranded nucleic acid molecule can be labelled with biotin, avidin or streptavidin, using art recognized techniques, and the solid support modified in turn, to be coated with biotin (if the nucleic acid molecule is labelled with avidin or streptavidin), or avidin/streptavidin (if the nucleic acid molecule is labelled with biotin). The art will be familiar with other pairings which result in effective bonding, including amination, thiophosphorylation, carboxylation, phosphorylation, amino silylation, addition of a thiol group, addition of an acrylamide, and so forth. In turn, the solid support can be treated to contain aldehyde groups (when the nucleic acid is aminated), to be coated with poly L lysine (when the nucleic acid is thiophosphorylated), aminated (when the nucleic acid molecule is carboxylated or phosphorylated), treated to contain one or more of isothiocyanate, epoxide, or carboxylic acid groups (also when the nucleic acid is aminated), phosphorylated (when the nucleic acid contains an amino silane moiety), mercaptopropylsilane or amino silane, linked by heterobifunctional cross linkers (when the nucleic acid has been modified to contain sulfide), acrylamide monomers (when the nucleic acid contains an acrylamide), and other pairings which will be known to the skilled artisan.

It should be pointed out that it is not necessary that the solid phase be functionalized with only one of the systems referred to supra. Further, it should be understood that since more than one end of one strand of a multistranded nucleic acid molecule may be modified, any number of various combinations of modifications on the multistranded molecules are possible and are contemplated. For example, a triplex nucleic acid molecule contains three 5' ends, and three 3' ends, leaving six possible sites for modification. Anywhere from 1 to 6 of the ends may be modified, using anywhere from 1 to 6 different modifiers. Generally, a multistranded nucleic acid molecule of "n" strands contains 2n termini, and anywhere from 1 to 2n of these may be modified, using anywhere from 1 to 2n modifiers.

As was pointed out, supra, all types of nucleic acid molecules can be attached to solid supports as described in the specification. Different configurations of nucleic acid molecules can be immobilized including B-DNA, Z-DNA, and so forth. The nucleic acid molecule can also be a nucleoprotein complex, a nucleochemical complex, a nucleodrug complex, a photocleaved nucleic acid molecule, and other structures which will be known to the skilled artisan. These molecules may be treated to make them more or permanently stable, such as by brominating Z-DNA, for example.

The type of solid support used can vary. All of the solid support materials known to the acid, such as glass, plastics such as polystyrene, and nylon membranes may be used.

A further feature of the invention is the use of solid supports which have been treated in particular ways to render them more receptive to both nucleic acid molecules and other types of molecule. In one embodiment, a solid support, such as glass or plastic, is scratched, etched or otherwise has its surface eroded, to produce a complex, three dimensional surface that is amenable to complete immobilization of a molecule, such as a nucleic acid or protein.

In a further embodiment, surfaces such as a plastic surface can be functionalized by ultraviolet radiation, again to facilitate complete immobilization of molecules, such as nucleic acid molecules or proteins. "Complete" immobilization is to be contrasted to the one-end immobilization referred to supra, in that in complete immobilization, the entire surface of the molecule is immobilized. One may consider this as a "horizontal" type of immobilization, as compared to "vertical" immobilization, as occurs supra. In addition to the nucleic acid molecules described supra, proteins, such as antibodies, including antibodies specific for the B form configuration of DNA, and other proteins such as DNA binding proteins, including zeta crystallin, can be so immobilized, other proteins, and other molecules may be so immobilized, and such molecules will be known to the skilled artisan.

Other features of the invention will be recognized by the artisan, and need not be reiterated here.

7. The method of claim 5, wherein said plastic has been scratched to present a 3 dimensional surface.

8. The method of claim 5, wherein said plastic has been treated by ultraviolet radiation.

9. The method of claim 1, wherein said modifying comprises treating at least one terminus of said multistranded nucleic acid molecule so that it is not hybridized to another nucleic acid molecule strand.

10. A method for immobilizing a multistranded, non-denatured nucleic acid molecule to a solid support, comprising treating the entire surface of one strand of said multistranded nucleic acid molecule to render the entire multistranded nucleic acid molecule bindable to said solid support and contacting said multistranded nucleic acid molecule to said solid support under conditions favoring immobilization thereto.

11. The method of claim 1, wherein said multistranded nucleic acid molecule comprises a peptide nucleic acid molecule, a nucleoprotein complex, a nucleochemical complex, a nucleodrug complex, or a photocleaved nucleic acid molecule.

12. The method of claim 11, wherein said photocleaved nucleic acid molecule comprises a metal chiral complex.

13. The method of claim 1, wherein said nucleic acid molecule is Z-DNA.

14. The method of claim 13, wherein said Z-DNA has been treated to render it permanently stable as Z-DNA.

We claim:

1. A method for immobilizing a multistranded, non-denatured nucleic acid molecule comprising at least 3 nucleic acid molecule strands to a solid support, comprising modifying a portion of each strand of said multistranded, non-denatured nucleic acid molecule to render it bindable to said solid support via all of said modified strands of said multistranded non-denatured nucleic acid molecule, and contacting said multistranded nucleic acid molecule to said solid support under conditions favoring immobilization thereto.

2. The method of claim 1, comprising aminating a terminus of at least one strand of said multistranded non-denatured nucleic acid molecule.

3. The method of claim 1, wherein said modifying comprising adding a biotin, avidin or streptavidin molecule to at least one strand at a terminus.

4. The method of claim 1, wherein said solid support comprises glass.

5. The method of claim 1, wherein said solid support comprises plastic.

6. The method of claim 1, wherein said solid support comprises a nylon membrane.

15. The method of claim 1, wherein said nucleic acid molecule is B-DNA.

16. The method of claim 1, wherein said multistranded nucleic acid molecule is circular.

17. The method of claim 1, wherein at least a portion of said nucleic acid molecule is supercoiled.

18. The method of claim 1, wherein said solid support contains aldehyde groups and said modifying comprises aminating two or more strands of said multistranded nucleic acid molecule.

19. The method of claim 1, wherein said solid support is coated with poly-L-lysine and said modifying comprises thiophosphorylating two or more strands of said multistranded nucleic acid molecule.

20. The method of claim 1, wherein said solid support has been aminated and said modifying comprises carboxylating or phosphorylating two or more strands of said multistranded nucleic acid molecule.

21. The method of claim 1, wherein two or more strands are of said multistranded nucleic acid molecule aminated and said solid support has been activated with isothiocyanate, aldehyde, epoxide, or carboxylic acid.

22. The method of claim 1, wherein said solid support has been phosphorylated and said two or more strands of said multistranded nucleic acid molecule have been modified by an amino silane moiety.

23. The method of claim 1, wherein at least two strands of said multistranded nucleic acid molecule have been modified by a thiol group, and said solid support contains mercaptopropylsilanes or amino silanes which have been linked by a heterobifunctional crosslinker.

24. The method of claim 1, wherein at least two strands of said multistranded nucleic acid molecule have been modified by a disulphide, and said solid support has been modified by mercaptosilane or amino silane linked by a heterobifunctional crosslinker.

25. The method of claim 1, wherein said solid support contains acrylamide monomers and at least two strands of said multistranded nucleic acid molecule contains an acrylamide.

26. Apparatus useful in analyzing molecular function, comprising a solid support which has been activated by ultraviolet laser irradiation and has a plurality of covalently bound multistranded nucleic acid molecules comprising at least three nucleic acid molecule strands affixed thereto, or has been treated by etching or scratching to present a three dimensional structure receptive to molecular binding thereto, and has a plurality of multistranded nucleic acid molecules comprising at least three nucleic acid molecule strands bound thereto, by at least two strands of said multistranded nucleic acid molecules.

27. The apparatus of claim 26, wherein said solid support comprises a nylon membrane.

28. The apparatus of claim 27, wherein said nylon membrane is attached to a glass or plastic support.

29. The apparatus of claim 28, wherein said multistranded nucleic acid molecules are B-DNA or Z-DNA.

30. A method for immobilizing a multistranded nucleic acid molecule comprising at least three nucleic acid molecule strands of interest, comprisng contacting said multistranded nucleic acid molecule to the apparatus of claim 26, to immobilize said molecule thereto.

31. The method of claim 29, wherein said molecule is immobilized fully.

32. The method of claim 5, wherein said plastic has been scratched to present a 3 dimensional surface and has been treated by ultraviolet radiation.

33. A method fbr immobilizing a plasmid to a solid support, comprising contacting said plasmid to at least one oligonuclcetide which has been modified at its 5' or 3' and to render it bindable to said solid support, wherein said plasmid and oligonucleotide form a triplex DNA structure, and stabilizing said triplex structure with benzoquinoquinoxaline.

34. The method of claim 33, further comprising adding psoralen to said stablizing agent to stabilize said triplex structure.

35. The method of claim 10, comprising treating the entire surface of each strand of said multistranded nucleic acid molecule.

* * * * *